United States Patent
Schrader

[19]

[11] Patent Number: 5,807,111
[45] Date of Patent: Sep. 15, 1998

[54] ORIENTATION AID

[76] Inventor: Jens Schrader, Landhausstr. 116, 70190 Stuttgart, Germany

[21] Appl. No.: 749,319

[22] Filed: Nov. 14, 1996

[30] Foreign Application Priority Data

Nov. 16, 1995 [DE] Germany ............ 195 42 678.9

[51] Int. Cl.⁶ .................................................. G01C 22/00
[52] U.S. Cl. .......................... 434/112; 434/116; 434/114; 367/116
[58] Field of Search ...................... 434/112, 116, 434/113, 114; 135/84, 85; 364/561; 367/116; 342/24; 250/552, 553

[56] References Cited

U.S. PATENT DOCUMENTS

| | | | |
|---|---|---|---|
| 2,590,052 | 3/1952 | Stuits ........................................ | 135/85 |
| 3,654,477 | 4/1972 | Benjamin ................................. | 250/552 |
| 4,025,922 | 5/1977 | Trawick .................................... | 342/24 |
| 4,280,204 | 7/1981 | Elchinger ................................. | 367/116 |
| 4,958,651 | 9/1990 | Najm ......................................... | 135/85 |
| 4,991,126 | 2/1991 | Reiter ....................................... | 364/561 |
| 5,358,461 | 10/1994 | Baily ........................................ | 482/124 |

Primary Examiner—Richard J. Apley
Assistant Examiner—Glenn E. Richman
Attorney, Agent, or Firm—Bachman & LaPointe, P.C.

[57] ABSTRACT

The invention relates to an orientation aid for visually impaired and particularly blind persons. In this connection, at least one signal device (5, 6) for the indicating of a change in the direction of walking is associated with a memory (7) for the storing of a selectable direction of walking.

4 Claims, 3 Drawing Sheets

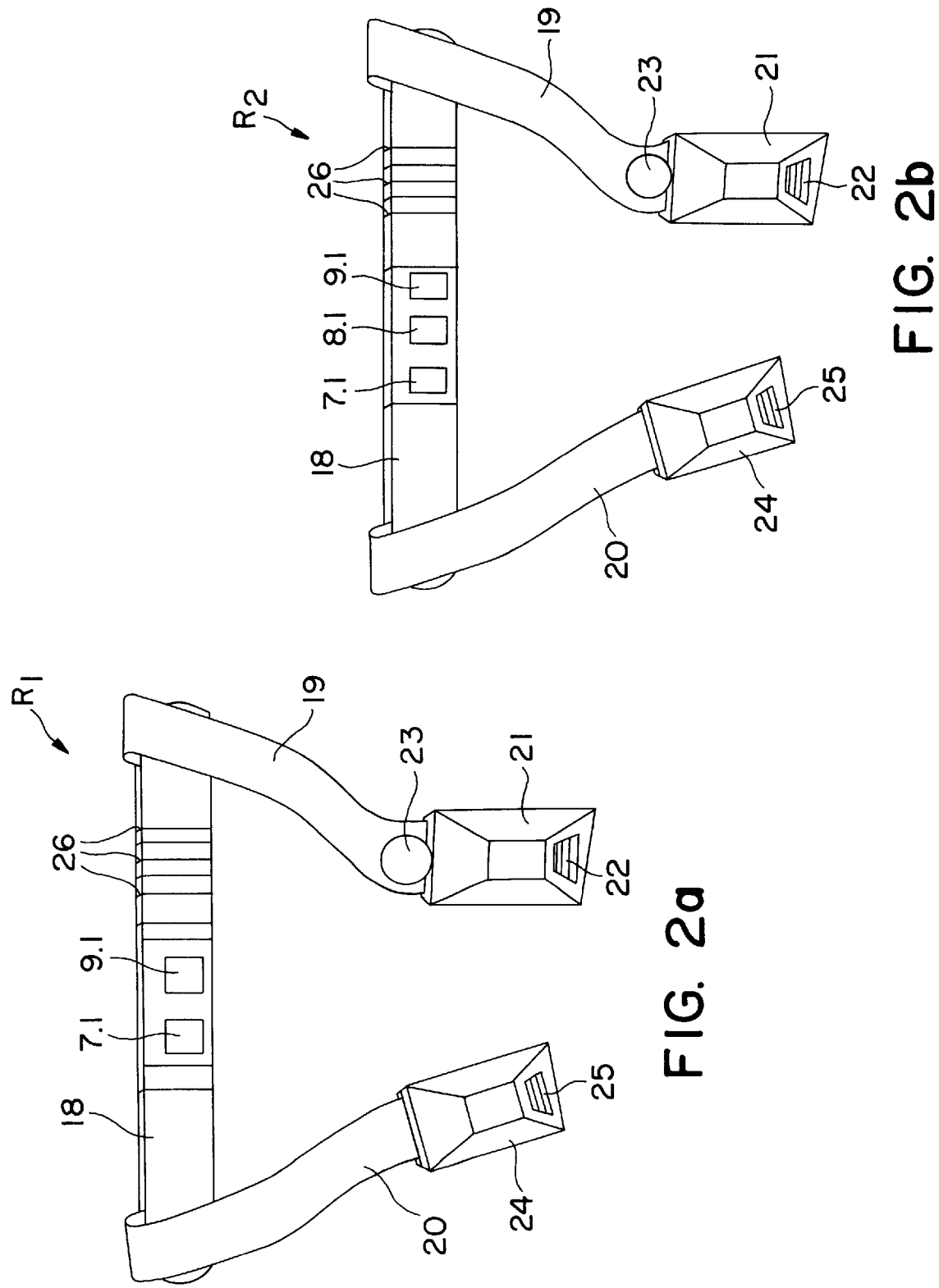

ORIENTATION AID

BACKGROUND OF THE INVENTION

The present invention relates to an orientation aid for visually impaired and particularly blind persons.

Such aids in orientation are known and customary on the market in various forms and embodiments. In particular, a simple cane is known by which a blind person senses a pathway, a house wall, a road, stairs, or similar obstacles. Such canes have the disadvantage that while they permit one to note obstacles in the lower region between hip and foot, there is a certain uncertainty with respect to obstacles in the region of the upper body and head, and the blind person must rely solely on his sense organs and reflexes. Therefore, there is a great danger of blind people injuring themselves on obstacles of this height upon movement.

Furthermore, blind persons must, when walking, rely on groping their way along sidewalks, roads, walls, and the like, by means of a cane so that only in this way can a path in a given direction be ascertained. However, sidewalks, walls or house walls are not always present as aids in groping and direction. For example, crossing a street is very difficult for the blind, since the direction towards the other side of the street must be maintained precisely without any guidance. Furthermore, it is not possible to walk a straight line without guidance.

The object of the present invention is to provide an orientation aid which eliminates the above-indicated disadvantages and with which a straight path upon walking can be maintained and which protects a region of the upper body directly in front of the body from obstacles.

SUMMARY OF THE INVENTION

In order to achieve this object, a memory for the storing of a selected direction of walking has, associated with it, at least one signal device which indicates a change from such direction.

This invention makes it possible for a compass, arranged preferably in the rear part of a belt, particularly in the vicinity of the spine, to recognize a given direction of walk. In order that this recognition can be converted into electrical signals, the compass is preferably developed as an electric compass. Furthermore, there are associated with the belt of the orientation aid at least two signal devices which are preferably arranged to the right and the left of the belt buckle. If the compass is lined up in a desired direction of travel, a coordinate is stored, after the alignment, in a processor which is also associated with the belt, if desired. Upon walking, the processor then continuously compares the actual value of the compass with the value stored and, upon a change, transmits a signal to one or the other signal device. If the actual deviation of the coordinate or deviation in direction upon walking is greater than the value stored, then, depending on the arrangement of the signal devices, one of the two is actuated so that the blind person knows precisely in what direction he must go in order to again return to the desired direction which has been stored. This is advantageous, in particular, upon crossing streets, paths, meadows, or the like, since the blind person has no possibility there of orienting himself, for instance, by means of sidewalks, walls, or the like.

The signal devices, which are operated by a preferably rechargeable battery, can transmit signals to the body by means of vibrators, in which connection, however, acoustic signals over loudspeakers or electric signals by electrical stimuli directly on the skin can also be used.

The belt is preferably made of elastic material, in which connection all parts, such as battery, compass and signal devices, are electrically connected to each other within the belt and can be worn under a sweater and possibly even on the skin.

In a further embodiment of the present invention, an orientation aid is created which rests by means of straps and side straps around the region of the neck on the shoulder. In this connection, the side straps extend over the shoulders, the strap resting, in the rear, in the region of the nape of the neck on the shoulder. Compass, processor, battery and similar devices are also arranged there. In the front region, right and left signal transmitters are arranged on the side straps, they being provided with switches. One of the two switches serves for the connecting or disconnecting of the orientation aid while the other switch optionally selects the type of signal which is indicated there, either electrical, electromechanical or acoustic.

In addition, a sensor which monitors a front region in front of the blind person is associated with at least one of the signal transmitters. The sensor can be developed as an infrared and/or ultrasonic or microwave or similar sensor. The object of the sensor is to monitor, in particular, the upper region of the body, shoulder and region of the head, and to indicate to the blind person by means of an acoustic, electric or electromechanical signal that an obstacle is present in the region in front of his upper body.

This region, or the range of this sensor, is intentionally selected very small, i.e. ranges of between 0.5 and 1.5 meters in front of the region of the upper body. Only in this way does the blind person have the possibility of not being influenced by obstacles which are at a greater distance away. In addition, a compass which also fulfills the functions described above can also be installed in this orientation aid.

For the simple operation of the orientation aid, a switch is provided on a cane, it taking over the activating of the direction indicator or the direction coordinate and storing it in the processor. The transmission to the processor is effected by radio, infrared radiation, or the like.

Furthermore, it lies within the scope of the present invention to use in such an orientation aid a GPS system which, after a given selection of coordinates or a given target can indicate the direction to the blind person via the signal transmitters. At the same time, walking on a straight line is supported by the compass.

BRIEF DESCRIPTION OF THE DRAWINGS

Further advantages, features, and details of the invention will be evident from the following description of preferred embodiments, read with reference to the drawing, in which:

FIGS. 2a and 2b are views in perspective of other embodiments of the orientation aid of FIG. 1;

DETAILED DESCRIPTION

Figure 1:
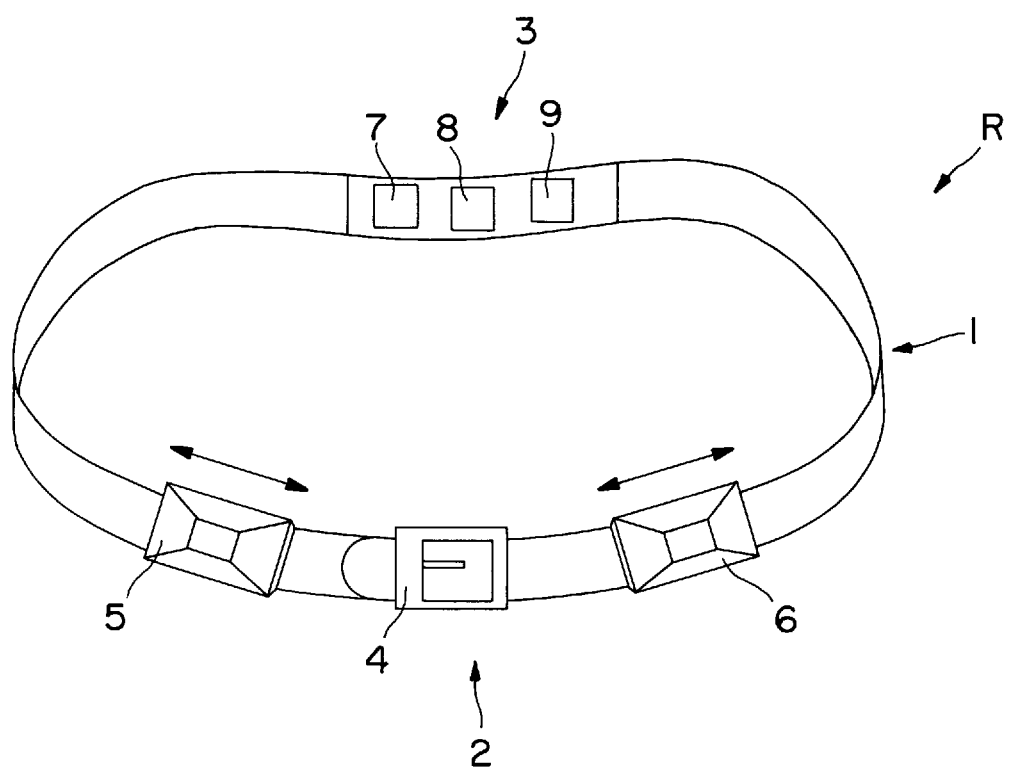
FIG. 1 is a perspective view of an orientation aid in accordance with the invention.

Referring to FIG. 1, an orientation aid R in accordance with the invention has a belt 1 which is divided into a front region 2 and a rear region 3. The belt 1 is adapted to be placed around a human body, particularly in the region of the hips. In this connection, the front region 2 is to lie against the stomach and the rear region 3 against the back of the human body. The opposite is also possible.

In order that the belt 1 can be placed around the human body, it must first be opened by means of a buckle 4, and then again closed. Of course, a continuous adjustment of the size of the belt also lies within the scope of the invention, so that the belt can be adapted to bodies of different size.

In the front region 2, to the right and left of the buckle 4, spaced uniformly apart, the belt 1 has signal devices 5 and 6. The signal devices 5, 6 are connected to a processor 7 via an electric connection (not shown in detail here) which extends in the rear region 3 within the belt 1 which is preferably developed in a soft and cushioned manner. The processor 7, which is arranged in the rear region 3, receives signals from an electric compass 8 arranged in the center alongside thereof. Furthermore, the signal devices 5, 6, the processor 7, and the electric compass 8 are fed by a preferably rechargeable battery 9 which is arranged in the rear region 3.

The manner of operation of the present invention is as follows:

It is particularly difficult for blind persons to maintain a given direction, particularly upon walking, if they, for instance, do not have any direction-indicating information or guides such as pavements, house walls, etc. However, particularly upon crossing streets or intersections where there is neither a pavement nor a house wall or the like, it is of great importance for the blind that they be guided directly across the street and that they cross it over the shortest path.

However, walking on a straight path, for instance along a straight street, can also be easily effected with the orientation aid of the invention.

The electrical compass 8 which is preferably arranged centrally in the belt 1, and therefore near the spine of the human body, transmits, when desired, upon a signal the actual coordinate in the compass 8 in the direction of walking or travel of the human body to the processor 7.

This coordinate is stored upon a given signal which is produced by a switch (not shown in detail) on the belt 1 or on one of the signal devices 5, 6. This stored coordinate is then used as reference coordinate for the following or varying coordinates upon walking in a different direction as basis of measurement.

If the continuous coordinate which is measured in the electric compass 8 differs now upon walking from the stored coordinate, a signal is transmitted to the signal device 5 or 6 depending on the deviation, whether positive or negative. These signal devices 5, 6 are to transmit the signals to the blind person in the form of a vibratory noise which can be directly felt on his skin or body. If the direction now differs from the direction originally stored, the blind person thereby changes his direction of walking, either to the right or to the left depending on which signal device 5, 6 transmits the corresponding signal until the direction originally stored has been reached again.

If a new signal is required as directional reference for a new indication of direction, the blind person directs himself in the direction in which he would like to go and again actuates the processor 7 which stores the desired direction of travel or direction coordinate of the electric compass 8 as reference in the processor 7. Then upon walking, differences which are transmitted by the electric compass 8 to the processor 7 and recognized are indicated on the signal devices 5 and 6 in the manner described above, so that the blind person knows in what direction he must go in order to maintain the desired direction. If the deviations between stored direction coordinate and actual direction coordinate upon walking are very slight, then the signal device 5, 6 does not operate. This tolerance should be adjustable here.

However, it also resides within the scope of the invention for the signal devices 5, 6 to give off acoustic tones which may also have different pitches, so that the blind person immediately recognizes that he must move in a direction to the right or the left.

There are also possible electric signal devices 5, 6 which, for instance, by means of electric currents, produce a prickling sensation on the skin of the human body so that the blind person also notes what direction he must take in order to re-establish the desired direction which was previously stored and maintain it. It is advantageous here that, in this way, no noise is produced and that the blind person can concentrate on the noises in his surroundings.

Figure 4:
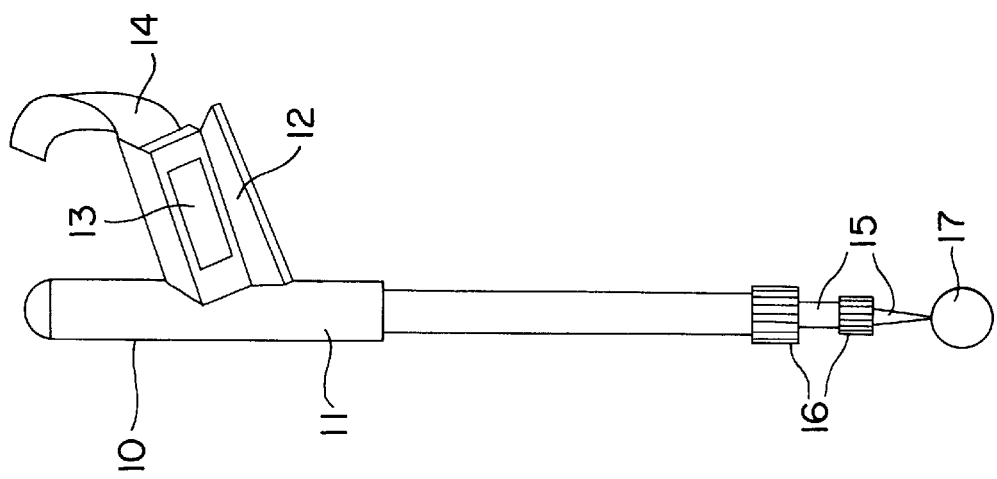
FIG. 4 shows a cane in accordance with the invention.

The depressing of a button on a switch 13 contained on a cane 10, as shown in FIG. 4, can also store a desired direction of travel. The cane 10 has a handle 11 with which a guide element 12 having the switch 12 is associated. The guide element 13 furthermore has a band 14 which, for instance by the insertion of flexible metals or the like, can be adapted to the shape of the wrist. Thus, the cane lies in the hand resting lightly, dependably and in guided manner on the wrist. The switch 13 is actuated by a finger of a hand so that, at that moment, the direction coordinate is stored in the processor 7. Renewed pressure on this switch 13 disconnects the orientation aid R.

In order that the blind person always recognizes the switch function which is operative at the time, so-called high/low switches are used, the on or off condition of which can be recognized by the position of the switch. Other switches, such as toggle switches, can also be used here.

The signal from the switch 13 is transmitted—not shown in detail here—by radio, infrared radiation, or the like to the belt 1. In such case, the belt 1 would be provided with a corresponding receiver.

In order that the cane 10 be developed so that it is variable for use by persons of different height, it has telescopic extensions 15 which can be fastened to the handle 11 in any extracted position by means of fastening elements 16. At the end of the cane 10 there is arranged, at the tip of the cane, a ball 17 which is easily turnable around the axis of the cane and which facilitates swinging without the sensor functions being limited.

Figure 3:
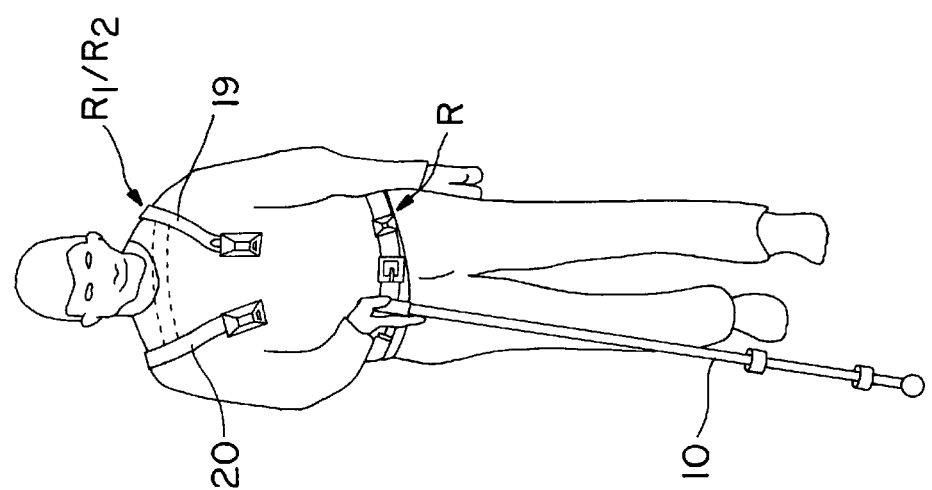
FIG. 3 is a view of an orientation aid in accordance with FIGS. 1, 2a and 2b, shown in position of use.

In a further embodiment of the present invention, shown in FIG. 2a, the orientation aid RI has a rear strap 18 which passes into side straps 19 and 20. In this case, strap 18, as well as side straps 19, 20, are made of elastic materials, for instance padded Goretex containing bendable elements. The orientation aid R1 can in this way be adapted to the shape of the shoulder. In that case, the strap 18 lies against the back, while the side straps 19 and 20 grip over the shoulder of a human body, as shown in FIG. 3.

Since the electric compass 8 in the strap 18 of the belt 1 is fixed in the plane of the back, it is thus easily possible to determine, perpendicular to the plane of the back and therefore in the forward direction of walking, this directional coordinate.

In that case, it can also be seen how the orientation aid R is fastened around the stomach or hips of the human body. The orientation aid, to be sure, can be worn unseen under one's clothing. On the other hand, the orientation aid R1 preferably lies on the shoulders of the blind person and has at the same time an optical function, since by developing it of lustrous or reflecting colors the blind person can be seen more easily in the dark by bicyclists, automobiles and persons close by.

So that the strap 18 can be adapted to shoulders of different width, slides 26 which can be flexibly pushed together or pulled apart are provided in the strap 18. In order, for instance, to reduce a width of the strap 18, these slides can be pushed together, it being also possible to remove them.

The orientation aid R1 has, in the front region of the side strap 19, a signal transmitter 21 with switch 22 which is connected to a preferably round to semi-spherical or spherical sensor 23 and is connected with the signal transmitter 21 or 24 via electric connections, not shown in detail here, to a processor 7.1 arranged in the strap 18. A second signal transmitter 24 is associated with the side strap 20, which is also provided with a switch 25.

It is essential here that the sensor 23, which may be developed as infrared, ultrasonic or other sensor, signals from obstacles which are present in a region of about 0.5 to 1.5 meters in front of the sensor 23 are recognized both in height and in width corresponding to the region of the upper body by said sensor 23 (sic).

This signal is transmitted to the processor 7.1, which is fed by a battery 9.1, in which connection a warning signal can be given by the signal transmitter 21, 24 in the form of a tone, steady tone, or the like.

The blind person is in this way warned that there is an obstacle right in the region of his upper body and can adjust himself accordingly to it.

However, it is also essential that the range of the sensor 23 can be limited to a minimum of about 0.5 to 1.5 meters, since otherwise obstacles at a greater distance away would only confuse the blind person with respect to the orientation or warning.

The orientation aid R1 is turned on by means of the push-button switch 22. In the event that an obstacle is detected by the sensor 23, an acoustic signal, connected by the switch 25, is optionally produced in the signal transmitters 21, 24, or else some other indication or some other signal, for example a mechanical vibration in the form of a vibrator, is produced. Vibrators are particularly suitable as signal transmitters 21, 24, since they are light and nevertheless readily felt, so that surrounding noises cannot be impaired thereby and particularly not heard by blind people.

In a further embodiment, according to FIG. 2b, there is shown an orientation aid R2 which is developed as identical part corresponding to orientation aid R1, but with the difference that, in addition, an electric compass 8.1, which is described in FIG. 1, is furthermore connected in the strap 18. This electric compass 8.1 assumes the same functions as the orientation aid R of FIG. 1, in which case also, by actuation of the switch 13 of the cane 10 (FIG. 4), the connecting or storing of the present orientation is possible, in which connection the deviation from the stored value is acoustically or electromechanically indicated in the signal transmitters 21 or 24, depending on the change in direction. Thus, in this case, the blind person can, in addition, as described in FIG. 1, use the orientation aid R2 also as direction indicator.

However, it is also within the scope of the present invention for a GPS system to form part of the orientation aid R. R1 or R2. In such case, a fixed, predetermined programmed direction can be called up which then, via the signal devices 5, 6 or signal transmitters 21, 24, provides the blind person with the way to his target.

I claim:

1. An orientation device for the visually impaired comprising:

support means for supporting;
    (1) processor means for storing a desired direction of travel and signalling deviation from said desired direction;
    (2) electronic compass means for determining actual direction of travel; and
    (3) a pair of spaced apart tactile signal means selectively actuated by said processor means when said processor means determines travel deviation for alerting the visually impaired to change direction to the left or right depending on which of the pair of tactile signal means is actuated;

said support means includes means for locating the support means on the visually impaired to form a loop wherein said pair of spaced apart tactile signal means defines therebetween a section of the loop and said electronic compass means is located on said section between said pair of tactile signal means.

2. An orientation device according to claim 1 wherein said means for locating includes securing means for forming a closed loop when said securing means is secured wherein said spaced apart tactile signal means define a front section of the closed loop and a rear section of the closed loop and said electronic compass means is located on the rear section.

3. An orientation device according to claim 2 wherein said securing means is located on the front section.

4. An orientation device according to claim 1 further including a cane including switch means on the cane for selecting the desired direction of travel stored by said processor means.

* * * * *